United States Patent [19]
Whittingham

[11] Patent Number: 5,413,556
[45] Date of Patent: May 9, 1995

[54] PHACOEMULSIFICATION HANDPIECE

[75] Inventor: William F. Whittingham, Foothill Ranch, Calif.

[73] Assignee: Inventive Systems, Inc., Irvine, Calif.

[21] Appl. No.: 112,450

[22] Filed: Aug. 27, 1993

Related U.S. Application Data

[63] Continuation of Ser. No. 831,460, Feb. 5, 1992, abandoned.

[51] Int. Cl.⁶ .............................................. A61B 17/20
[52] U.S. Cl. .................................... 604/22; 604/30; 606/107; 606/169
[58] Field of Search ................ 604/22, 27, 30, 35; 606/33, 107, 128, 169

[56] References Cited

U.S. PATENT DOCUMENTS

| | | |
|---|---|---|
| 3,589,363 | 6/1971 | Banko . |
| 4,014,333 | 3/1977 | McIntyre . |
| 4,169,984 | 10/1979 | Parisi . |
| 4,386,927 | 6/1983 | Eichenbaum . |
| 4,516,398 | 5/1985 | Wuchinich ............................ 604/22 |
| 4,533,957 | 11/1985 | Williams et al. . |
| 4,573,979 | 3/1986 | Blake . |
| 4,578,059 | 3/1986 | Fabricant et al. . |
| 4,652,255 | 3/1987 | Martinez . |
| 4,737,148 | 4/1988 | Blake . |
| 4,804,364 | 2/1989 | Dieras et al. ........................ 604/22 |
| 4,808,154 | 2/1989 | Freeman . |
| 4,897,079 | 1/1990 | Zaleski et al. . |
| 4,904,238 | 2/1990 | Williams . |
| 4,909,249 | 3/1990 | Akkas et al. . |
| 5,038,756 | 8/1991 | Kepley ................................ 604/22 |
| 5,162,044 | 11/1992 | Gahn et al. ...................... 606/169 X |

Primary Examiner—David H. Willse
Assistant Examiner—Mary Beth O. Jones
Attorney, Agent, or Firm—Curtis, Morris & Safford

[57] ABSTRACT

A surgical device is provided which emulsifies body tissue, irrigates the surgical site with a saline solution, and removes fluids and tissue, via aspiration from the surgical site. More specifically, a surgical handpiece is provided which is particularly suited to be utilized for the removal of cataractous tissue from the eye. In order to prevent cross-contamination of tissue, the surgical device herein incorporates an easily detachable and disposable outer housing to facilitate thorough cleansing of the irrigation solution path and reduce the time and effort required for such cleaning. Moreover, a secure sealing system is provided in the area of the interface between the inner body portion of the handpiece and a stainless steel shell to prevent leakage and contamination of the irrigating solution.

24 Claims, 2 Drawing Sheets

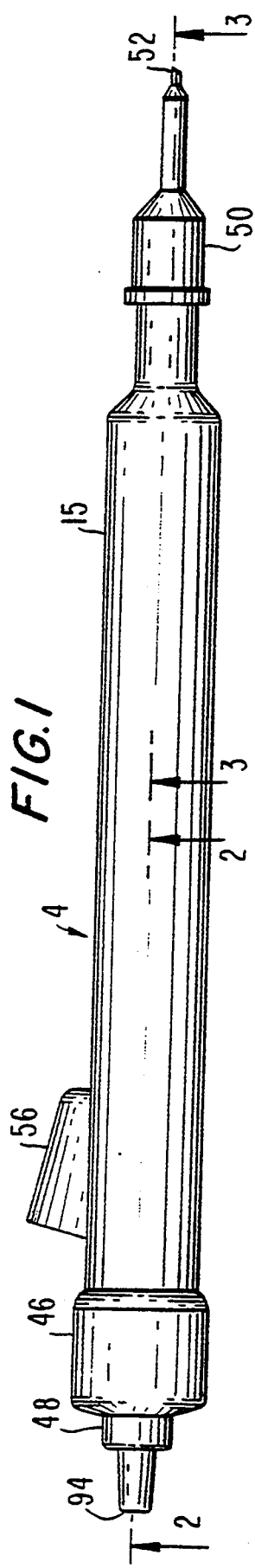
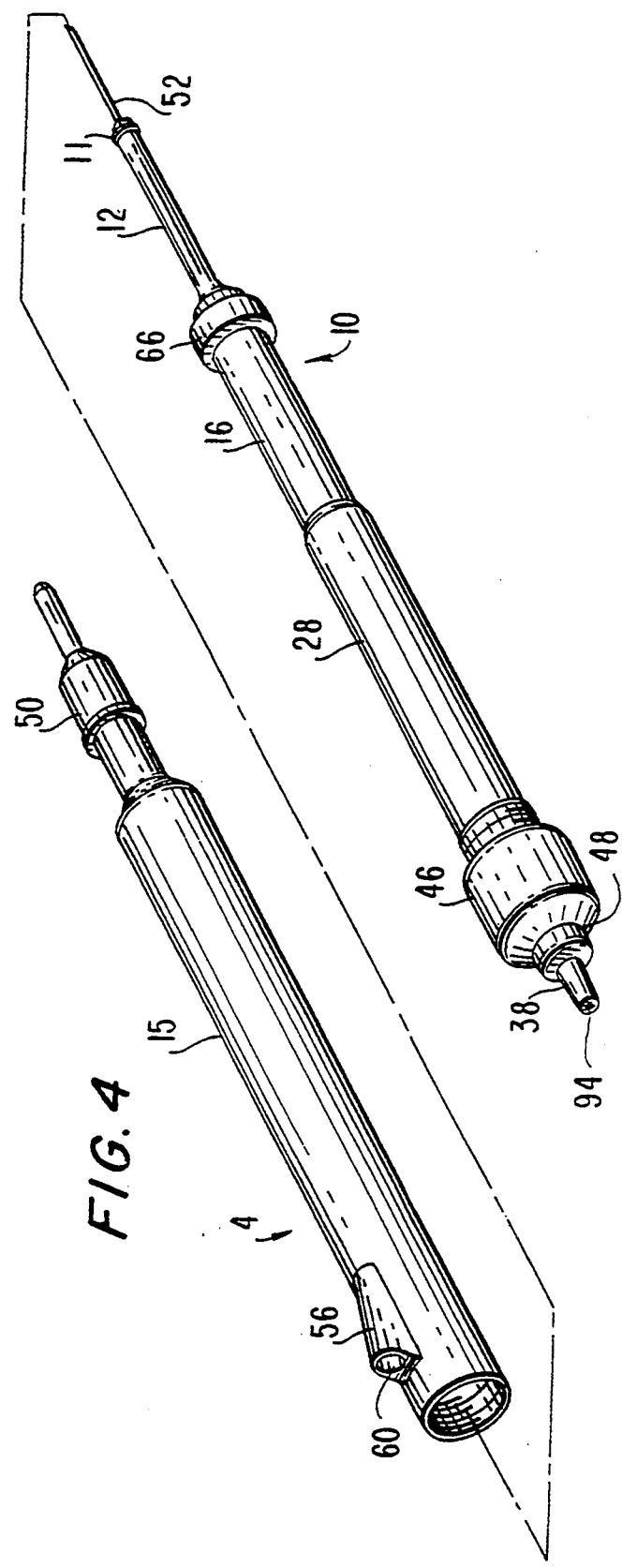

PHACOEMULSIFICATION HANDPIECE

This application is a continuation of application Ser. No. 07/831,460, filed Feb. 5, 1992, now abandoned.

FIELD OF THE INVENTION

The present invention pertains to cutting instruments used in surgery and, more specifically, to cutting instruments containing irrigation and aspiration features for the purpose of removal of cataractous and/or other tissue from the eye during surgery.

BACKGROUND OF THE INVENTION

Handpieces which incorporate cutting, aspirating and irrigating features are commonly used by ophthalmic surgeons during surgical operations on the eye. Because ocular surgery often involves cutting away or emulsifying unwanted tissues, as is the case in cataract surgery, the need often arises to remove tissues or fluids from the eye. To prevent damage to the eye tissue, there is also a need to irrigate the surgical site.

A number of attempts have been made to produce handpieces capable of effectively cutting, irrigating and aspirating the ocular surgical site. These instruments typically have an elongated cylindrical probe defining a cutter at their distal end, which may be inserted into the eye through an incision in the sclera. The delicate nature of ocular surgery requires that these probes be very narrow. The cutting tip of the probe is made to oscillate by means of a piezoelectric or magnarestrictive motor situated near the proximal end of the handpiece. The proximal portion of the handpiece, which must house a motor and drive mechanism, and which must be designed so as to be easily manipulated by the surgeon, is necessarily much thicker than the probe section. This difference in sizes causes the girth of the handpiece to severely narrow at a point approximately three fourths of the distance from the proximal end to the distal end of the instrument.

In order to transmit an irrigating saline solution to the probe, handpieces found in the prior art were equipped with a narrow groove cut through the solid metal outer body of the instrument. A similar groove was cut for the aspiration of fluids away from the surgical site. Due to the significant narrowing of the handpiece structure, these grooves followed a severely angular pathway through the handpiece.

A number of significant problems have been experienced with prior art handpieces. For example, the oscillating nature of the cutting tip causes cavitation of the saline solution, forming bubbles which are flushed into the eye by the flow of saline solution through the irrigation pathway. Because such bubbles impede a surgeon's view of the surgical site, they interfere with and slow down surgical procedures. Second, pulsating action, caused by the pump which flushes saline solution into the eye on the aspiration side of the handpiece, causes the eyeball to flutter during surgery and also interferes with surgical procedures.

Most importantly, the angular nature of both the irrigation pathway and the aspiration pathway makes thorough cleaning of the handpiece extremely difficult if not impossible. Thorough cleaning has now become a critical issue in light of contemplated government regulations which deal strictly with the prevention of cross tissue contamination.

In the first phase of a project by the present applicant to enhance the efficacy of prior art handpieces ("Phase I"), two significant improvements were achieved. First, the aspiration pathway was run straight through the center of the handpiece eliminating the cleaning problem caused by this formerly angular pathway. The new straight pathway can be simply cleaned by means of a straight brush or wire.

Second, rather than cutting a groove in the solid metal body or adding a tube on the outside of the piezoelectric motor or of the handpiece so as to create a pathway for irrigating saline solution, the present applicant created an outer body housing, or shell, fitting around the motor, drive mechanism, aspiration pathway and horn, such that irrigating solution could be introduced through a Luer fitting into an annular cavity between the housing and the titanium horn. This system creates a reservoir of significant volume near the site of cavitation, and thus, bubbles created by cavitation tend to migrate towards the top of the handpiece rather than being flushed out into the eye.

Though significant, the Phase I improvements did not solve the problem of how to thoroughly cleanse the irrigation pathway which, though altered from the prior art, remained angular and thus difficult to clean.

Further, in the Phase I improvement, cable connections were provided between the irrigating solution source and the irrigation pathway and the vacuum (aspiration source) and the aspiration pathway. As the handpiece is moved during surgical procedures, these cable connections may impede the surgeon's line of sight to the surgical site.

OBJECTS OF THE INVENTION

It is thus a primary object of the present invention to provide an improved phacoemulsification handpiece device which overcomes the disadvantages of the prior art.

It is another object of the present invention to improve applicant's Phase I invention by incorporating an easily detachable outer body housing to facilitate thorough cleansing of the irrigation solution path.

It is a further object of the present invention to provide a secure sealing system in the area of the interface between the outer body housing and the stainless steel shell to prevent leakage and contamination of the irrigating solution.

Yet another object of the present invention is to provide a phacoemulsification device which includes an economically disposable outer body housing unit to reduce the time and effort required for thorough cleansing of the handpiece.

It is yet a further object of the patent invention to provide a phacoemulsification handpiece device which includes a reservoir for the irrigating solution which effectively eliminates bubbles and pulsations in the eye.

It is a still further object of the present invention to provide a phacoemulsification handpiece which does not impede the surgeon's line of sight to the surgical site.

Various other objects and advantages of the present invention will become apparent to those persons of ordinary skill in the art from the foregoing description taken in conjunction with the accompanying drawings.

SUMMARY OF THE INVENTION

The current invention is a surgical device which emulsifies body tissue, irrigates the surgical site with a saline solution, and removes fluids and tissue, via aspiration, from the surgical site. This instrument is particularly suited to be utilized as a phacoemulsification device for the removal of cataracts (cataractous tissue) from the eye.

The device is generally cylindrical, tapering to a narrow width at the bottom of the instrument. The device consists of two primary structural components: the outer body housing, or shell, and the inner body. Like the shell, the inner body is cylindrical and tapers to the bottom.

The inner body is generally solid and is primarily comprised of a horn, a heel, a core, and a piezoelectric motor. At the top of the handpiece is the core, a cylindrical object, flared near its top, which serves, in part, to form a seal with the shell and also holds the horn, heel, piezoelectric crystals and electrodes together. The core is made from a rigid material such as stainless steel or other metal. Surrounding the core's narrow bottom is the heel, also made of rigid material such as titanium. The heel serves to add structural support to the device and to partially house the piezoelectric motor. Below the heel is the piezoelectric motor, consisting of two rings of piezo crystals sandwiching a ring-shaped electrode. The crystal rings and the electrode encircle a portion of the core directly below the heel. Below the piezoelectric motor is the horn, also made from titanium or other rigid metal. The horn surrounds the bottom-most portion of the core and continues downward, narrowing near the bottom of the device.

A disposable "phaco needle," the cutting and emulsifying tip of the instrument, is attached at the bottom of the horn. The phaco needle is made to vibrate by the action of the piezoelectric motor. A narrow shaft of generally constant width extends along the radial axis of the instrument and through the needle to provide an aspiration pathway.

The outer-body housing, or shell, is a thin-walled hollow cylinder which surrounds the inner body. The shell follows the same general contour as the outside of the inner-body, and is made from a rigid material such as metal or plastic. The inside top portion of the shell is threaded and can be screwed onto corresponding threads located on the outside of the flared portion of the core. A series of rubber O-rings act as seals at this connecting point.

A Luer fitting is mounted near the top of the shell. An aperture in the side of the shell allows saline solution to be pulled through the Luer fitting into the chamber created by the inner walls of the shell and the outer walls of the inner body. Water can flow down between the shell and the inner body of the instrument, through holes cut in a support ring, and into a disposable, silicone sleeve located at the bottom of the instrument. This irrigation pathway also provides for a self-cooling of the core, especially the crystal rings and the electrode of the piezoelectric motor. The sleeve funnels saline solution through small apertures near the vibrating tip of the phaco-needle, causing the surgical site to be irrigated. A peristaltic pump is attached at the top of the instrument, drawing a partial vacuum through the aspiration pathway to evacuate fluid and tissue from the surgical site.

The present phacoemulsification handpiece device also provides the surgeon with an unimpeded line of sight to the surgical site. By simply rotating the outer shell with respect to the core by virtue of corresponding interior and exterior threads, the surgeon can orient the handpiece such that the cable connections to the irrigations and aspirations pathway do not impede the surgeon's line of sight.

During surgery, body tissue sometimes migrates into the irrigation reservoir of the handpiece, thereby contaminating it. However, the present invention allows the outer body housing of the handpiece to be easily detached. This provides the ability to quickly and thoroughly clean the handpiece.

Another advantage of the present invention is that the outer body housing can be made from an economically disposable plastic or similar material, completely obviating the need to even clean the housing.

BRIEF DESCRIPTION OF THE DRAWINGS

The foregoing features and advantages of the invention are explained in greater detail in the preferred embodiment and in the description of the accompanying drawings, in which:

FIG. 1 is a front elevational view of a phacoemulsification handpiece device in accordance with a preferred embodiment of the present invention.

FIG. 4 is a front perspective view of the phacoemulsification handpiece device of FIG. 1 specifically illustrating the shell separated from the body of the device.

DETAILED DESCRIPTION OF THE PREFERRED EMBODIMENT

Figure 2:
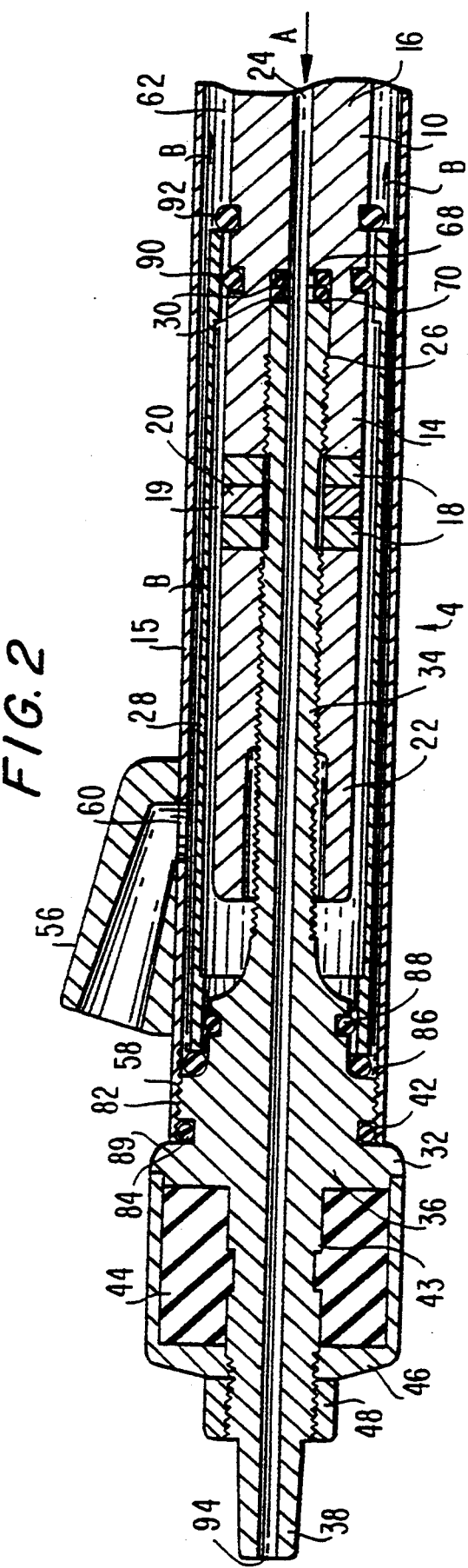
FIG. 2 is a longitudinal cross-sectional view of the rear section of the phacoemulsification handpiece device taken along line 2—2 of FIG. 1.
Figure 3:
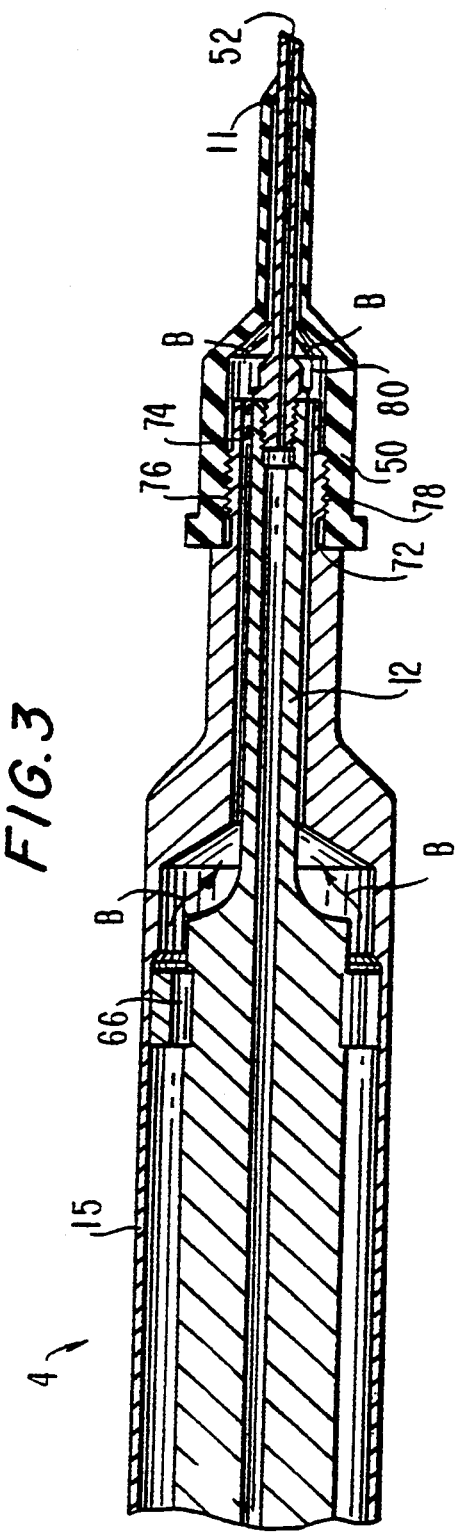
FIG. 3 is a longitudinal cross-sectional view of the front section of the phacoemulsification handpiece device taken along line 3—3 of FIG. 1.

Referring now to the FIGS. 1 through 4, wherein like reference numerals designate like parts in the several views, a phacoemulsification handpiece device 4 for the removal of cataractous and/or other tissue from the eye in accordance with the present invention is provided. As is shown in FIGS. 2 through 4, the central portion of the handpiece 4 of the present invention is an elongated, generally cylindrical shaft otherwise known as the horn 10. The horn extends from a point near the center of the handpiece 4 to the bottom (distal) end 11 of the handpiece 4. At a point near its bottom, the outer radius of the horn 10 rapidly decreases to a narrow, constant width. This region is defined by the horn stem 12. The inner radii of the horn stem 12 and horn body 16 (the region between the upper horn 14 and the horn stem 12), defines the lower portion of an aspiration pathway 24 and has a constant diameter throughout. Since the horn decreases in diameter to the horn stem 12, the surgeon's line of sight into the surgical site is enhanced.

Integral with the horn 10 are two narrow rings containing piezo crystals 18. An electrode 20 is sandwiched between the two piezo crystal rings 18 such that it achieves physical contact with the rings 18. In combination, the crystal rings 18 and electrode 20 form a piezoelectric motor 19. Current for the piezoelectric motor is provided by an external source (not shown). Extending above the top of the piezoelectric motor 19 is an elongated ring, or tube, preferably made from titanium, forming the heel 22.

Surrounding the upper horn 14, the two sets of piezo crystals 18, the electrode 20 and the heel 22 is a horn cover 28. The horn cover 28 is preferably made of stainless steel or a rigid polymer, such as delrin, and functions to encase and insulate the electrical components contained therein. As will be explained in more detail below, the horn cover 28 also serves an important role in the sealing of the handpiece 4.

The inner radii of the horn stem 12, the horn body 16 and a core 32 define a straight and unobstructed pathway 24 for aspiration flow. A vacuum is drawn in the direction of arrows "A" in FIG. 1 through this pathway 24 to remove fluids and tissues from the body.

The core 32, is a generally cylindrical member, which, at its bottom half, matingly fits and screwed inside a sheath 26 created by the open central portion of the upper horn 14. Thus, the core 32 holds the upper horn 14, heel 22, crystal rings 18 and electrode 20 together. Two relatively small O-rings 30 fit over a small extension 68 of the core 32. These rings 30 are radially centered about the longitudinal axis of the handpiece and abut a shoulder section 70 which constitutes a stepped surface down to the lower diameter of the extension 68. The O-rings 30 limit direct metal-to-metal contact between the core 32 and the horn 19 and serve to absorb vibrational shock and prevent damage to the metallic parts.

The upper end of the core 32 consists of two functional regions, a middle core 36 and an upper core stem 38. The outer radius of the middle core 36 increases in a stepped fashion to accommodate fittings with a shell 15, the horn cover 28 and O-rings 42. A notch 43 (see FIG. 2) is cut into the upper core stem 38 to accommodate a ring of electrical insulation 44 which acts to insulate the user from any possible electric shock emanating from the crystal rings 18 and electrode 20. The electrical insulation 44 is also used for electrical cable connection. A cap 46 is fit over the electrical insulation 44 and mates with the middle core 36. A cap lock 48 retains the cap in it preferred position, as shown in FIG. 2.

The shell 15, which is a tubular outer body housing, encases the horn stem 12, horn body 16, crystal rings 19 and electrode 22. A Luer fitting 56 is mounted on the shell 15 towards the top of the handpiece 4. This fitting 56 provides communication between the outside of the handpiece 4 and an irrigation reservoir or pathway 62 through an aperture 60 cut in the shell 15. The shell 15 and Luer fitting 56 are made from a rigid material, preferably a disposable material, such as plastic. The aperture 60 allows an irrigating solution to pass into the irrigation reservoir 62 which is defined by a cavity located between the shell 15 and the horn cover 28, the sheath 26, the horn body 16 and the horn stem 12. The irrigating fluid passes through the irrigating reservoir 62 in the direction of arrows "B" in FIG. 2 and 3. Since the irrigating solution passes over the horn, including the crystal rings 18 and the electrode 20 of the piezoelectric motor, the irrigation pathway assembly provides for a self-cooling of the phacoemulsification handpiece.

A centering ring 66, preferably made of teflon if the body 16 is formed of a metal, is attached around the horn body 16 and provides an offset from the horn body 16 to maintain the shell in a centered, concentric position in relation to the aspiration pathway 94. The outer periphery of the centering ring is ribbed (not shown) to provide a standoff from the horn body, yet still allowing the flow of liquid through the irrigation reservoir 62.

A disposable sleeve 50, which is preferably formed of silicone and thus biologically inert, fits over the bottom, narrowed portion of the shell 15. The sleeve 50 has an upper lip 72 and a lower shoulder 74 which respectively fit into a circumferential notch 76 and around a ridge 78. The sleeve 50 surrounds a disposable surgical ("phaco") needle 52 which acts as the cutting implement of the handpiece 4. The disposable phaco needle 52 widens at its base to fit snugly in a receptive axial bore 80 at the bottom end of the horn stem 12. The sleeve 50 projects downwardly from the bottom of the shell 15 surrounding the majority of the phaco needle 52. Ultimately, the irrigating fluid exits the irrigation reservoir 62 from one or more ports (not shown) in the sleeve 50 to irrigate the tissue.

The shell 15 also contains interior threads 58 which mate with corresponding threads 82 located at the exterior upper end of the middle core. A first O-ring 42 located in a groove 84 in the core 32, acts between the shell 15 and the core 32 to form a first seal. A cushion 86 and a second O-ring 88 act to form a seal between the cover 28 and core 32 to prevent ingress of the irrigation solution to the piezoelectric motor area. A third O-ring 90 and a lock ring 92 are provided for the same purpose and act in the same manner as the cushion 86 and second O-ring 88, but at the opposite end of the sheath 26.

In accordance with one of the general objects of the present invention, the present phacoemulsification handpiece device also provides the surgeon with an unimpeded sightline to the surgical site. As aforementioned, during use, the interior threads 58 of the shell 15 are engaged with corresponding threads 82 on the exterior of the middle core 36 of the horn 10 until the shell is retarded from further lateral movement by the shoulder section 89 of the middle core 36. If, however, the surgeon's sightline is impeded by the cable connections to the aspiration or irrigation pathways or the electrical connection to the piezoelectric motor, the threads are of a sufficient length such that the surgeon can rotate the outer shell relative to the core section such that the shell is rotated in any angular position up to a 180° orientation to provide a clear unimpeded sightline for the surgeon to the surgical site.

In accordance with another object of the present invention, the shell 15 may be detached from the horn 10 for cleaning (see FIG. 4). In order to separate the shell 15 from the horn 10, the interior threads 58 of the shell 15 are disengaged from the threads 82 of the middle core section of the horn. The various O-ring seals permit this cleaning without running the risk of damage to the crystal rings 18 and electrode 20. The ability to remove the shell 15 and clean the irrigating solution reservoir 62 allows the complete decontamination of the reservoir 62 on both its inner and outer surfaces. In fact, if desired, the shell 15 can be made of a disposable plastic or other similar material to obviate the need for its cleaning.

In use, the handpiece 4 is initially connected to an external source of an irrigating (usually saline) solution. The source of irrigating solution is connected to the irrigation reservoir 62 via the Luer fitting 56. The solution then travels through the handpiece 4 in the manner set forth by arrows "B" in FIGS. 2 and 3, essentially between the shell 15 and the cover 28 for the horn 10. The solution flows out through the terminal end of the sleeve 50 to irrigate the surgical work surface and flush away extraneous matter.

Similarly, the handpiece 4 is connected to an external vacuum (aspiration) source at the upper core stem 38. The vacuum acts by way of a longitudinal pathway 94 through the central axis of the handpiece 4, including the needle 52. As the needle cuts tissue and the like, at least some of the matter is drawn through the longitudinal pathway 94 to keep the surgeon's work area clear.

The application of current from a source (not shown) to the electrode ring 20 causes the piezo crystals 18 to vibrate. This vibration, in turn, causes the horn 10, heel 22 and correspondingly the attached needle 52, to vibrate. The vibration is isolated from the shell 15 by the construction of the core 32 as a separate piece from the horn 10. It is further isolated by the damping effect of O-rings 30.

In accordance with FDA regulations to prevent cross contamination, the handpiece 4 must be cleaned prior to re-use. The present invention permits the removal of the shell 15 to provide direct access to the irrigation reservoir 62 for cleaning. The shell 15 is simply unscrewed from threads 58 of the core 32. The shell 15 is then either thrown away or cleaned and screwed back into place. The longitudinal (aspiration) pathway 94 of the handpiece can be advantageously cleaned by using a straight brush (not shown) since the pathway 94 is itself straight. The needle 52 and the sleeve 15 are simply discarded and replaced with identical pieces.

While the present invention has been particularly shown and described with reference to certain preferred embodiments, it will be readily apparent to those of ordinary skill in the art that various changes and modifications may be made therein without departing from the spirit and scope of the invention. It is intended that the appended claims be interpreted as including the foregoing as well as various other such changes and modifications.

What is claimed is:

1. A phacoemulsification handpiece device for cutting body tissue from a surgical site and providing for aspiration and irrigation during surgery, said phacoemulsification handpiece device comprising:
   cutting means for cutting body tissue;
   drive means, connected to said cutting means, for providing power to said cutting means;
   an irrigation pathway for facilitating the flow of fluid to irrigate an area of body tissue to be cut by said cutting means;
   an aspiration pathway extending through said drive means for facilitating the application of vacuum to the area of body tissue to be cut by said cutting means; and
   an outer shell covering said drive means and defining said irrigation pathway formed by a generally annular space between said outer shell and said drive means, said outer shell being separably attached to said drive means to expose substantially all of said irrigation pathway for facilitating the cleaning of said irrigation pathway and freely rotatable with respect to said drive means such that the sight lines of the surgeon to the surgical site are unimpeded.

2. An apparatus according to claim 1, wherein said outer shell is disposable.

3. An apparatus according to claim 2, wherein said outer shell is formed of a plastic material.

4. An apparatus according to claim 1, wherein said outer shell is formed of stainless steel.

5. An apparatus according to claim 1, wherein fluid flows into said irrigation pathway through a Luer fitting which is mounted on said outer shell.

6. An apparatus according to claim 7, wherein said outer shell is disposable.

7. An apparatus according to claim 6, wherein said outer shell is plastic.

8. A phacoemulsification handpiece device for cutting body tissue from a surgical site and providing for aspiration and irrigation during surgery, said phacoemulsification device comprising:
   cutting means for cutting body tissue;
   a horn member including drive means, connected to said cutting means, for providing power to said cutting means, and an aspiration pathway extending therethrough for facilitating the application of vacuum to the surgical site; and
   an outer shell covering said horn member and forming a generally annular space between said outer shell and said horn member which defines an irrigation pathway which allows irrigating fluid to flow to said surgical site, said outer shell being separably attach to said horn member to expose substantially all of said irrigation pathway to facilitate the cleaning of said irrigation pathway and freely rotatable with respect to said horn member such that the sight lines of the surgeon to the surgical site are unimpeded.

9. The phacoemulsification handpiece device of claim 8 wherein said drive means includes an electrode being sandwiched between a pair of piezo crystal rings thereby forming a piezoelectric motor.

10. The phacoemulsification handpiece device of claim 8 wherein said outer shell is disposable.

11. The phacoemulsification handpiece device of claim 10 wherein said outer shell is formed of a plastic material.

12. The phacoemulsification handpiece device of claim 8 wherein said cutting means is a disposable phaco needle extending outwardly from said horn member and supported by a disposable silicone sleeve member fitting over said horn member.

13. The phacoemulsification handpiece device of claim 12 wherein said horn member narrows in diameter toward an end thereof from which said needle extends to thereby enhance the sightline of the user to the surgical site.

14. The phacoemulsification handpiece device of claim 8 wherein said aspiration pathway is provided straight through said horn member to facilitate cleaning thereof.

15. A phacoemulsification handpiece device for cutting body tissue from a surgical site and providing for aspiration and irrigation during surgery; said phacoemulsification device comprising:
   cutting means for cutting body tissue;
   a horn member including drive means, connected to said cutting means, for providing power to said cutting means, and an aspiration pathway extending therethrough for facilitating the application of vacuum to the surgical site;
   an outer shell covering said horn member and forming a generally annular space between said outer shell and said horn member which defines an irrigation pathway which allows irrigating fluid to flow to said surgical site, said outer shell being separably attached to said horn member to expose substantially all of said irrigation pathway to facilitate the cleaning of said irrigation pathway; and
   said horn member being freely rotatable with respect to said outer shell to permit rotation thereof in any angular position in a 180° orientation such that the sight lines of the surgeon to the surgical site are unimpeded.

16. A phacoemulsification handpiece device for cutting body tissue from a surgical site and providing for aspiration and irrigation during surgery, said phacoemulsification device comprising:
   cutting means for cutting body tissue;
   a horn member including drive means, connected to said cutting means, for providing power to said cutting means, and an aspiration pathway extending therethrough for facilitating the application of vacuum to the surgical site;
   an outer shell covering said horn member and forming a generally annular space between said outer shell and said horn member which defines an irrigation pathway which allows irrigating fluid to flow to said surgical site, said outer shell being separably attached to said horn member and freely rotatable therewith to expose substantially all of said irrigation pathway to facilitate cleaning of said irrigation pathway; and
   means for maintaining said outer shell in a centered, concentric position in relation to said aspiration pathway, said maintaining means being attached around said horn member.

17. The phacoemulsification handpiece device of claim 16 wherein said maintaining means is a centering ring extending into the irrigation pathway thereby providing an offset of said horn body with respect to said outer shell.

18. The phacoemulsification handpiece device of claim 17 wherein the outer periphery of said centering ring is ribbed to allow the flow of irrigating fluid through said irrigation pathway.

19. A phacoemulsification handpiece device for cutting body tissue from a surgical site and providing for aspiration and irrigation during surgery, said phacoemulsification handpiece device comprising:
   cutting means for cutting body tissue;
   drive means, connected to said cutting means, for providing power to said cutting means;
   an irrigation pathway for facilitating the flow of fluid to irrigate an area of body tissue to be cut by said cutting means;
   an aspiration pathway extending through said drive means for facilitating the application of vacuum to the area of body tissue to be cut by said cutting means; and
   an outer shell covering said drive means and defining said irrigation pathway formed by a generally annular space between said outer shell and said drive means, said outer shell being separably attached to said drive means to expose substantially all of said irrigation pathway for facilitating the cleaning of said irrigation pathway and freely rotatable with respect to said drive means such that the sight lines of the surgeon to the surgical site are unimpeded, said outer shell being threaded to mate with a horn member, wherein said horn member defines a portion of said aspiration pathway.

20. An apparatus according to claim 19, wherein said outer shell abuts an O-ring when it is threaded onto said horn member, such that a liquid tight seal is formed.

21. An apparatus according to claim 20, wherein said outer shell is disposable.

22. A phacoemulsification handpiece for cutting body tissue from a surgical site and providing for aspiration and irrigation during surgery, said phacoemulsification device comprising:
   cutting means for cutting the body tissue;
   a horn member including drive means, connected to said cutting means, for providing power to said cutting means, and an aspiration pathway extending therethrough for facilitating the application of vacuum to the surgical site;
   an outer shell covering said horn member and forming a generally annular space between said outer shell and said horn member which defines an irrigation pathway which allows irrigating fluid to flow to said surgical site, said outer shell being separably attached to said horn member to expose substantially all of said irrigation pathway to facilitate cleaning of said irrigation pathway; and
   means for maintaining said outer shell in a centered, concentric position in relation to said aspiration pathway, said maintaining means being attached around said horn member and being in the form of a centering ring extending into the irrigation pathway thereby providing an offset of said horn member with respect to said outer shell, and wherein the outer periphery of said centering ring is ribbed to allow the flow of irrigating fluid through said irrigation pathway.

23. A phacoemulsification handpiece device for cutting body tissue from a surgical site and providing for aspiration and irrigation during surgery, said phacoemulsification device comprising:
   cutting means for cutting body tissue;
   a horn member including drive means, connected to said cutting means, for providing power to said cutting means, and an aspiration pathway extending therethrough for facilitating the application of vacuum to the surgical site;
   an outer shell covering said horn member and forming a generally annular space between said outer shell and said horn member which defines an irrigation pathway which allows irrigating fluid to flow to said surgical site, said outer shell being separably attached to said horn member to expose substantially all of said irrigation pathway to facilitate the cleaning of said irrigation pathway and freely rotatable with respect to said horn member such that the sight lines of the surgeon to the surgical site are unimpeded, and
   wherein said drive means includes an electrode being sandwiched between a pair of piezo crystal rings thereby forming a piezoelectric motor and said irrigation pathway surrounds said horn member and said piezocrystal rings to provide for self-cooling of the horn member.

24. A phacoemulsification handpiece device for cutting tissue from a surgical site and providing for aspiration and irrigation during surgery; said phacoemulsification device comprising:
   cutting means for cutting body tissue;
   a horn member including drive means, connected to said cutting means, for providing power to said cutting means, and an aspiration pathway extending therethrough for facilitating the application of vacuum to the surgical site;
   an outer shell covering said horn member and forming a generally annular space between said outer shell and said horn member which defines an irrigation pathway which allows irrigating fluid to flow to said surgical site, said outer shell being separably attached to said horn member to expose substantially all of said irrigation pathway to facilitate the cleaning of said irrigation pathway;

said horn member being freely rotatable with respect to said outer shell to permit rotation thereof in any angular position in a 180° orientation such that the sight lines of the surgeon to the surgical site are unimpeded; and interior threads provided on said outer shell matingly engageable with exterior threads on said horn member which are of a sufficient length such that when engaged the user can rotate said outer shell relative to said horn member such that said outer shell can be rotated in any angular position in a 180° orientation.

* * * * *

UNITED STATES PATENT AND TRADEMARK OFFICE
CERTIFICATE OF CORRECTION

PATENT NO. : 5,413,556
DATED : May 9, 1995
INVENTOR(S) : William F. Whittingham

It is certified that error appears in the above-identified patent and that said Letters Patent is hereby corrected as shown below:

In claim 6, line 65 (Col. 7, line 65), change "7" to --5--.

In claim 8, line 16 (Col. 8, line 16), change "attach" to --attached--.

Signed and Sealed this

Eighteenth Day of July, 1995

Attest:

BRUCE LEHMAN

Attesting Officer      Commissioner of Patents and Trademarks